United States Patent [19]

Wüst

[11] Patent Number: 4,591,647
[45] Date of Patent: May 27, 1986

[54] PROCESS FOR THE PRODUCTION OF 2,2'-DIBENZOTHIAZOLYL DISULPHIDE

[75] Inventor: Alfredo Wüst, Roesrath, Fed. Rep. of Germany

[73] Assignee: Bayer Aktiengesellschaft, Leverkusen, Fed. Rep. of Germany

[21] Appl. No.: 641,528

[22] Filed: Aug. 16, 1984

[30] Foreign Application Priority Data

Aug. 19, 1983 [DE] Fed. Rep. of Germany ....... 3329976

[51] Int. Cl.$^4$ .............................................. C07D 277/78
[52] U.S. Cl. ...................................... 548/157; 548/158
[58] Field of Search ................................ 548/157, 158

[56] References Cited

U.S. PATENT DOCUMENTS 2,304,426 12/1942 Sibley ..................................... 548/158
4,482,720 11/1984 Kaplan ................................... 548/158

FOREIGN PATENT DOCUMENTS 684715 4/1964 Canada .
2800462 7/1978 Fed. Rep. of Germany .

OTHER PUBLICATIONS

The Merck Index 9th Edition (1976) p. 1115.

Primary Examiner—Donald G. Daus
Assistant Examiner—Robert Benson
Attorney, Agent, or Firm—Sprung Horn Kramer & Woods

[57] ABSTRACT

2,2'-dibenzothiazolyl disulphide produced from an alkali metal salt of 2-mercaptobenzothiazole by oxidation using chlorine is obtained substantially free from acid by-products if oxidation is carried out under such conditions that the reaction mixture still contains at least 2.5%, by weight, of the alkali metal salt of 2-mercaptobenzothiazole at the end of the reaction.

5 Claims, No Drawings

PROCESS FOR THE PRODUCTION OF 2,2'-DIBENZOTHIAZOLYL DISULPHIDE

The economically most important process for the production of 2,2'-dibenzothiazolyl disulphide is the oxidation of aqueous alkali metal salt solutions of 2-mercaptobenzothiazole using chlorine or mixtures of chlorine and air. In order to obtain high yields and satisfactory degrees of purity from this reaction, it is necessary to keep the reaction conditions within certain limits since acidic by-products are liable to be produced by over-oxidation, especially at high pH-values, while at low pH values, for example below 7, mercaptobenzothiazole precipitates, undergoing virtually no oxidation owing to its low solubility in water, and equally contaminates the desired end product.

To overcome these disadvantages, German Offenlegungsschrift Nos. 2,309,584 and 2,800,462, both in the name of American Cyanamide Co., propose the continuous introduction beneath the surface of a vigorously-stirred aqueous mixture of separate streams of an aqueous solution of an alkali metal salt of mercaptobenzothiazole, an aqueous solution of an alkali metal hydroxide and gaseous chlorine. The temperature of the reaction mixture during this procedure should be from 20° to 75° C., the pH from 6 to 10 and the redox potential of the aqueous mixture from −150 to 250 mV and the reaction should be carried out in such a manner that the concentration of the reactants during the whole reaction time is virtually zero. With this procedure, it is intended to achieve yields of over 97% and to use up not more than 20% of excess chlorine. It can be seen from the practical examples given that from 10 to 20 mol % of excess chlorine and from 10 to 20 mol % of alkali are used up, based in each case on the alkali metal salt of 2-mercaptobenzothiazole, and that, in spite of the complicated reaction procedure, from 1.7 to 2.9 mol % of over-oxidation products are produced and the end product still contains up to 1.1%, by weight, of free mercaptobenzothiazole.

The object of the present invention was to find a process for the oxidation of aqueous alkali metal solutions of 2-mercaptobenzothiazole using chlorine to produce a 2,2'-dibenzothiazolyl disulphide which would be substantially free from acid by-products and 2-mercaptobenzothiazole.

The problem was solved by carrying out the oxidation in such a manner that at least 2.5%, by weight, of the alkali metal salt of 2-mercaptobenzothiazole is still present in the reaction mixture at the end of the process.

The present invention therefore relates to a process for the production of 2,2'-dibenzothiazolyl disulphide by the oxidation of aqueous, from 8 to 50%, by weight, alkali metal salt solutions of 2-mercaptobenzothiazole using chlorine or chlorine/air mixtures at temperatures of from 15° to 60° C. and pH values of from 9 to 13, characterised in that the concentration of the alkali metal salt of 2-mercaptobenzothiazole is not less than 2.5%, by weight, at any time during the reaction.

The reaction may be carried out batchwise or continuously. In a continuous reaction, the steady concentration (=minimum concentration) of the alkali metal salt of mercaptobenzothiazole is preferably from 5 to 25%, by weight.

In a batchwise reaction, the concentration of the alkali metal salt of 2-mercaptobenzothiazole at the end of the reaction is preferably from 5 to 9%, by weight.

Particularly advantageous results are obtained when the pH of the reaction mixture is from 10 to 12.5. This is surprising since the above-mentioned German Offenlegungsschrifts specifically warn against pH values above 10.

Under the conditions indicated above, the acidic by-products content may be suppressed to below the limits of detectability and a storage stable and thermally stable 2,2'-dibenzothiazolyl disulphide which is in a very pure state, containing only minute quantities of 2-mercaptobenzothiazole, may be obtained in high yields. In the most favourable case, the chlorine consumption may be reduced to an excess of not more than 5 mol % and the consumption of alkali metal hydroxide may also be limited to a maximum of 5 mol%.

Unreacted alkali metal salts of 2-mercaptobenzothiazole are left in the aqueous solution on filtration of the desired end product and may be precipitated as 2-mercaptobenzothiazole by acidification, isolated and re-used or used for other purposes.

It is preferred to use the sodium salt of 2-mercaptobenzothiazole and to maintain the pH within the desired range by means of sodium hydroxide solution.

In the Tables given below, the various columns have the following meanings:

A: pH
B: initial concentration of NaMBT in %, by weight
C: final concentration of NaMBT in %, by weight
D: yield in %, based on reacted NaMBT
E: chlorine consumption in mol-%, based on NaMBT
F: NaOH consumption in mol-%, based on NaMBT
G: 2,2'-dibenzothiazolyl disulphide content in %, by weight
H: content in acid compounds in %, by weight, based on the isolated product
I: MBT content in %, by weight, based on the isolated product.

EXAMPLE 1

756 g of a 50%, by weight, solution of the sodium salt of 2-mercaptobenzothiazole (NaMBT), which has been purified by triple fractionated precipitation with hydrochloric acid and resolution of the middle fraction in sodium hydroxide solution, and 1248 g of deionised water are introduced into a thermostatically-controlled double-jacketed ground glass vessel of 3 liters capacity equipped with a stirrer, gas inlet frit, pH measuring electrode, thermometer, dropping funnel and reflux condenser. The solution contains 18.9% by weight of NaMBT.

A constant stream of a mixture of gaseous chlorine and air delivering 10 l/h of chlorine and 200 l/h of air is introduced at 35° C. At the same time, 344 g/h of the 50%, by weight, solution of NaMBT are added to maintain the NaMBT concentration constant at 18.9%, by weight. The pH is maintained constant at 10 by the addition of 10%, by weight, sodium hydroxide solution. The experiment is completed after 16 g of chlorine have been introduced. The precipitated 2,2'-dibenzothiazolyl disulphide is suction filtered, washed until neutral and dried under vacuum.

The yield is 74 g, corresponding to 99.8% of the theoretical yield, based on the quantity of NaMBT put into the process. The chlorine consumption is 101.2 mol-%, and the consumption of sodium hydroxide solution, 1 mol-%, based on the quantity of NaMBT introduced. The concentration of active substance is 98.5%, the concentration of acid constituents (expressed as benzothiazole sulphonic acid) is 0%, the free mercaptobenzothiazole content (MBT) is 1.4% and the melting point is 170.2°-172.8° C.

The same experiment carried out at pH 12 produces the following results:

Yield: 99%, chlorine consumption: 104.8%, sodium hydroxide consumption: 12%, concentration of active substance: 99.8%; acid concentration: 0%; concentration of free MBT: 0.2%, melting point: 174.9°-177.8° C.

EXAMPLES 2 TO 4

A constant NaMBT concentration is adjusted and maintained in the reaction vessel as in Example 1 by the introduction and further addition of the required quantities of NaMBT solution. The pH is maintained constant by the addition of sodium hydroxide solution. Chlorine and air are introduced as a mixture at a constant velocity.

The following yields and qualities are obtained at the different concentrations adjusted:

| EXAMPLE | A | B/C | D | E | F | G | H | I |
|---|---|---|---|---|---|---|---|---|
| 2 (a) | 10 | 8 | 98.9 | 104.0 | 1 | 99.1 | 0 | 0.8 |
| (b) | 12 | 8 | 98.5 | 107.0 | 14 | 99.7 | 0 | 0.1 |
| 3 (a) | 10 | 1.9 | 98.3 | 106.4 | 3 | 99.7 | 0.1 | 0.2 |
| (b) | 12 | 1.9 | 97.8 | 108.8 | 19 | 99.6 | 0.3 | 0 |
| 4 (c) | 10 | 0.2 | 95.7 | 112.8 | 11 | 98.5 | 0.7 | 0.2 |
| (b) | 12 | 0.2 | 94.5 | 133.7 | 59 | 97.2 | 0.9 | 0.2 |

EXAMPLE 5

195 kg of a 50%, by weight, NaMBT solution and 455 l of deionized water, corresponding to a 15%, by weight, solution, are introduced into an 800 l enamel vessel equipped with stirrer, chlorine inlet device, inflow apparatus for sodium hydroxide solution and circulating pump with pH measuring instrument, and the solution is heated to 35° C. 0.94 m$^3$/h of chlorine and 15.2 m$^3$/h of air are introduced in the form of a mixture at pH 10 with stirring. 15.4 kg of chlorine are introduced in the course of 5.2 hours. The dibenzothiazolyl disulphide is filtered off, washed free from chloride and dried. The mother liquid is acidified to pH 3 using hydrochloric acid and the precipitated 2-mercaptobenzothiazole is suction filtered, washed free from chloride and dried. The final concentration of NaMBT is 2.5%, by weight.

69.9 kg of 2,2'-dibenzothiazolyl disulphide and 14.0 kg of 2-mercaptobenzothiazole, corresponding to 83.3% conversion, are obtained. Yield: 98%; chlorine consumption: 103 mol-%, consumption of sodium hydroxide solution: 2 mol-%.

Concentration of active substance: 98.8%; acid content: 0%, concentration of free MBT: 1.2%; melting point: 173.4°-176.7° C.

EXAMPLE 6

50 kg of a 50%, by weight, NaMBT solution and 450 l of deionized water (5%, by weight, of NaMBT) are introduced into the apparatus described in Example 5 and heated to 35° C. 5.2 kg of chlorine (as a chlorine/air mixture) are introduced with stirring over 2 hours. The final concentration of NaMBT is 0.04%, by weight.

After the reaction mixture has been worked-up as in Example 5, 21.2 kg of 2,2'-dibenzothiazolyl disulphide and 0.15 kg of 2-mercaptobenzothiazole, corresponding to a conversion of 99.2%, are obtained.

Yield: 97.7%; chlorine consumption: 114 mol-%; consumption of sodium hydroxide solution: 9 mol-%.

Concentration of active substance: 98.04%; acid content 1.2%; concentration of free MBT: 0.8%; melting point: 168.4°-172.6° C.

EXAMPLE 7

A quantity of NaMBT solution corresponding to the hourly throughput is introduced into a 3-liter, ground glass vessel equipped with overflow, stirrer, gas inlet frit, dropping funnel and reflux condenser, and a chlorine/air mixture in proportions, by volume, of 1:20 is introduced for 1 hour. NaMBT solution is thereafter added continuously while chlorine/air mixture is introduced and the reaction product is removed at the overflow. The 2,2'-dibenzothiazolyl disulphide formed is removed from the reaction product every hour and the residue of mercaptobenzothiazole left in the mother liquor is precipitated using hydrochloric acid.

Details and results are given in the following Table.

TABLE 1

| | A | B | C | D | E | F | G | H | I |
|---|---|---|---|---|---|---|---|---|---|
| a | 12 | 14.1 | 0 | 97.4 | 110.4 | 15 | 98.7 | 0.7 | 0.8 |
| b | 11 | 8.8 | 0 | 94.6 | 120 | 50 | 96.5 | 1.8 | 0.9 |
| c | 12 | 8.8 | 3.0 | 98.5 | 115.3 | 36 | 98.9 | 0.6 | 0.3 |
| d | 12 | 8.8 | 5.5 | 99 | 118 | 42 | 99.2 | 0.1 | 0.5 |
| e | 11 | 14.1 | 4.0 | 99 | 103 | 4 | 99.7 | 0 | 0.2 |
| f | 12 | 35.8 | 6.5 | 98 | 105 | 14 | 98.7 | 0 | 1.2 |

I claim:

1. A process for the production of 2,2'-dibenzothiazolyl disulphide comprising oxidizing aqueous, from 8 to 50%, by weight, alkali metal salt solutions of 2-mercaptobenzothiazole using chlorine or chlorine/air mixtures at temperatures of from 15° to 60° C. and pH values of from 9 to 13, and maintaining a concentration of the alkali metal salt of 2-mercaptobenzothiazole such that at no time during the reaction does said concentration amount to less than 2.5%, by weight.

2. Process according to claim 1, characterised in that the reaction is carried out continuously with a steady concentration of the alkali metal salt of 2-mercaptobenzothiazole of from 5 to 25%, by weight.

3. Process according to claim 1, characterised in that the reaction is carried out batchwise and the concentration of the alkali metal salt of 2-mercaptobenzothiazole is from 5 to 9%, by weight, at the end of the reaction.

4. Process according to claim 1, characterised in that the pH of the reaction mixture is from 10 to 12.5.

5. A process according to claim 1, wherein the alkali metal is sodium.

* * * * *